(12) United States Patent
Brewer et al.

(10) Patent No.: US 7,333,854 B1
(45) Date of Patent: Feb. 19, 2008

(54) ORTHOSTATIC CARDIAC OUTPUT RESPONSE PACER FOR HEART FAILURE PATIENTS AND DIABETIC PATIENTS

(75) Inventors: James E. Brewer, Lino Lakes, MN (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 454 days.

(21) Appl. No.: 11/048,251

(22) Filed: Jan. 31, 2005

(51) Int. Cl.
*A61N 1/00* (2006.01)
(52) U.S. Cl. .............................. 607/18; 607/19; 607/27
(58) Field of Classification Search ............ 607/17–24, 607/9, 14, 27
See application file for complete search history.

(56) References Cited

U.S. PATENT DOCUMENTS

| | | | |
|---|---|---|---|
| 4,712,555 A | 12/1987 | Thornander et al. ........ | 128/419 |
| 4,788,980 A | 12/1988 | Mann et al. ................. | 128/419 |
| 4,940,052 A | 7/1990 | Mann et al. ................. | 128/419 |
| 5,466,254 A | 11/1995 | Helland ....................... | 607/123 |
| 5,476,483 A | 12/1995 | Bornzin et al. .............. | 607/17 |
| 6,314,323 B1 | 11/2001 | Ekwall ......................... | 607/23 |
| 6,625,493 B2 | 9/2003 | Kroll et al. ................... | 607/17 |
| 6,658,292 B2 | 12/2003 | Kroll et al. ................... | 607/19 |
| 6,738,666 B1 | 5/2004 | Park et al. .................... | 607/18 |
| 2002/0147476 A1 | 10/2002 | Daum ........................... | 607/17 |
| 2003/0040776 A1 | 2/2003 | Kroll et al. ................... | 607/9 |
| 2003/0045910 A1 | 3/2003 | Sorensen et al. ............. | 607/23 |

FOREIGN PATENT DOCUMENTS

EP 1 291 036 A2 3/2003

*Primary Examiner*—Mark Bockelman

(57) ABSTRACT

An exemplary method includes detecting a change in position, measuring cardiac output after the detecting a change in position and, based at least in part on the measuring cardiac output, deciding whether to increase a cardiac pacing rate. An exemplary method may rely on activity in lieu of or in addition to position to decide whether to increase a cardiac pacing rate. Various exemplary methods aim to compensate for orthostatic effects such as those associated with dysautonomia. Various other exemplary methods are disclosed along with various exemplary devices, systems, etc.

16 Claims, 12 Drawing Sheets

Dysautonomia
400

Case I: Normal   420

Case II: Sympathetic Failure (Orthostatic Hypotension)   424

Case III: Excessive Sympathetic   428

ORTHOSTATIC CARDIAC OUTPUT RESPONSE PACER FOR HEART FAILURE PATIENTS AND DIABETIC PATIENTS

TECHNICAL FIELD

Subject matter disclosed herein generally relates to cardiac pacing and/or stimulation therapy. Various exemplary mechanisms concern compensating for orthostatic effects or dysautonomia.

BACKGROUND

Dysautonomia is highly correlated with progressive CHF and renal disease such as those due to complications of diabetes. The correlation is due in significant part to side effects of various aggressive and long-term pharmacological treatments for CHF and diabetes. For example, diuretics are a mainstay of many CHF treatment regiments and orthostatic hypotension is known to be a progressive effect of excessive diuresis. More specifically, ACE inhibitors are known to cause or to worsen orthostatic hypotension.

With respect to the mechanics of underlying various orthostatic responses, consider that, in a supine position, approximately 25% to 30% of the circulating blood resides in the thorax. When a person assumes an upright position from a supine position, a gravity-mediated downward displacement of 300 ml to 800 ml of blood occurs to the abdomen and extremities. A change to an upright position thus causes a drop in blood volume of about 25% to 30% for regions that were flush with blood in the supine position, with 50% of this change occurring typically in the first few seconds of standing. This rapid redistribution of blood causes a decline of venous return to the heart and a decrease in cardiac filling pressure. In turn, stroke volume, and therefore cardiac output, declines approximately 40% due to the decline in venous return. In a normal individual, the decreased venous return to the heart can effect circulation in a manner that triggers baroreceptors in the carotid arteries and in the aortic arch, which, in turn, stimulate a sympathetic response and inhibit a parasympathetic response. Arteriolar constriction, venous constriction, increased skeletal muscle tone, and an increased heart rate are the normal hemodynamic responses to increased sympathetic tone caused by a drop in arterial pressure and cardiac output. Orthostatic stabilization is normally achieved in one minute or less, with a gradual tapering of heart rate.

With dysautonomia, the sympathetic nervous system may fail to respond adequately to decreasing blood pressure and, consequently, heart rate may not increase. This type of failure is an example characteristic of progressing dysautonomia. A patient with an inability to adjust to such position changes (i.e., impaired orthostatic stabilization) is often diagnosed as having orthostatic hypotension. If severe or otherwise problematic, a patient may be fitted with a pacing device capable of compensating for inadequate orthostatic control.

While various pacemakers are capable of compensating for inadequate orthostatic control, usually via enhanced rate responsive pacing (see, e.g., U.S. Pat. No. 6,351,642 and PACE 2000; 23 [Pt II]: 1809-1811, which are incorporated by reference herein), a need exists for improved mechanisms, especially for patients with progressing CHF. In particular, a need exists for algorithms that can respond to conditions prior to, during or after a change in position. As described herein, various exemplary methods, devices, systems, etc., address these need or other needs.

SUMMARY

An exemplary method includes detecting a change in position, measuring cardiac output after the detecting a change in position and, based at least in part on the measuring cardiac output, deciding whether to increase a cardiac pacing rate. An exemplary method may rely on activity in lieu of or in addition to position to decide whether to increase a cardiac pacing rate. Various exemplary methods aim to compensate for orthostatic effects such as those associated with dysautonomia. Various other exemplary methods are disclosed along with various exemplary devices, systems, etc.

In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary mechanisms (e.g., presented as methods, devices, systems, etc.) pertain generally to dysautonomia compensation. In particular, when a patient changes activity level or position, dysautonomia may cause or prevent proper, responsive cardiac function. Various types of dysautonomia are described as well as various exemplary mechanisms for compensation.

Exemplary Stimulation Device

The techniques described below are intended to be implemented in connection with any stimulation device that is configured or configurable to stimulate nerves and/or stimulate and/or shock a patient's heart.

Figure 1:
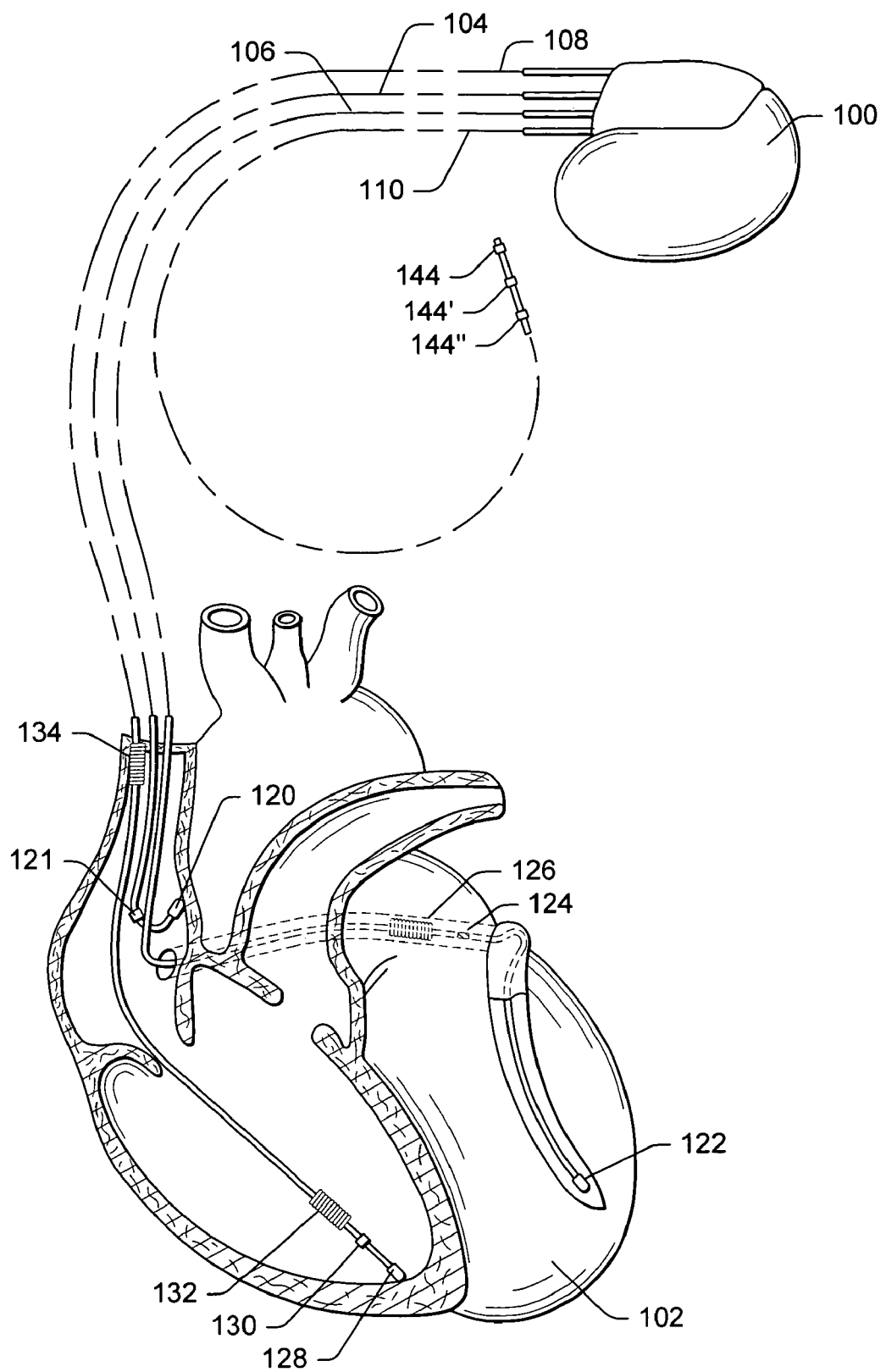
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
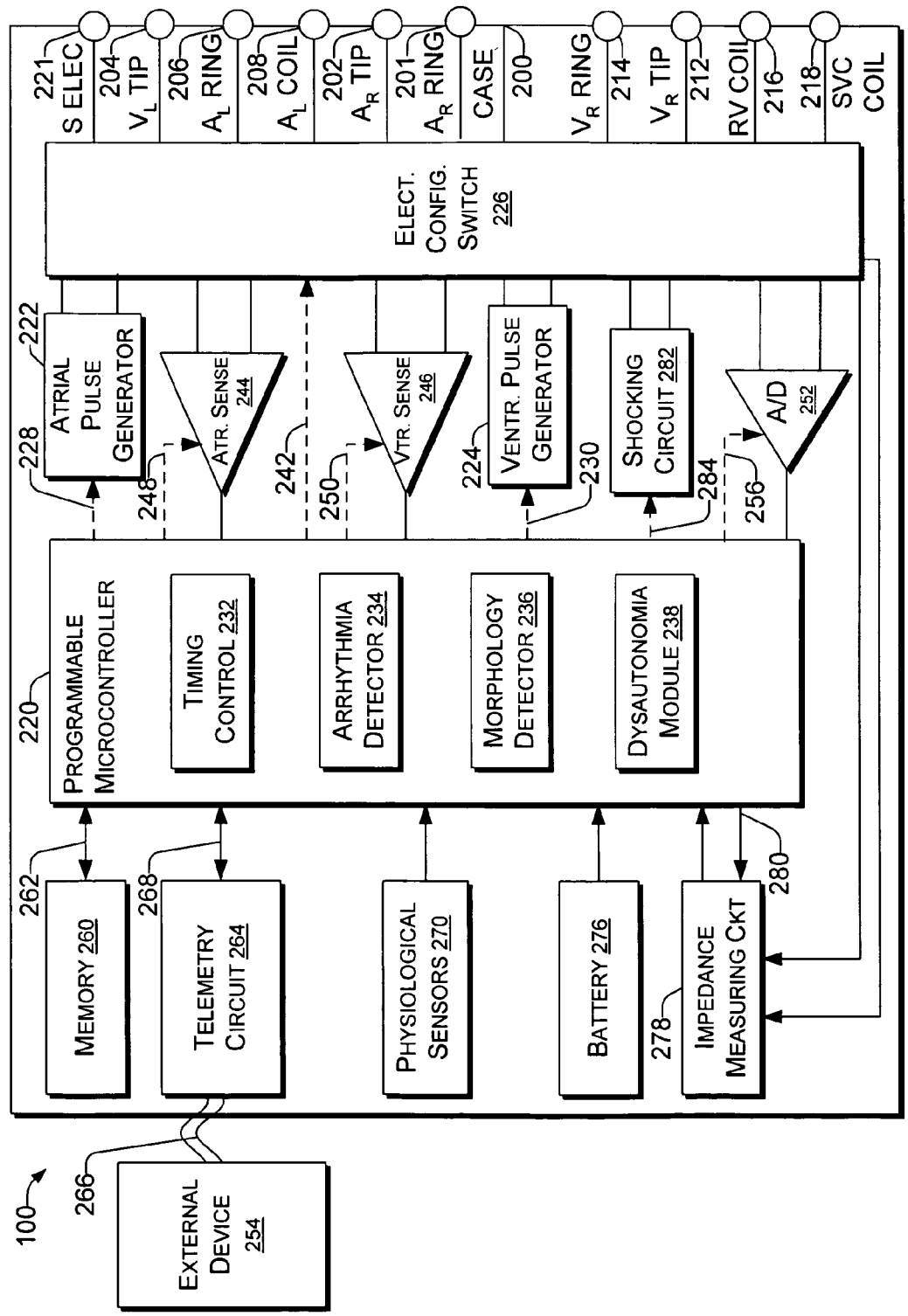
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally a minute ventilation (MV) response module (which is not shown in FIG. 2). These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation.

Microcontroller 220 further includes a dysautonomia module 238 for performing a variety of tasks related to compensation for dysautonomia. This component can be utilized by the stimulation device 100 for determining desirable times to administer various therapies, including, but not limited to, ventricular stimulation therapy, biventricular stimulation therapy, resynchronization therapy, atrial stimulation therapy, etc. The dysautonomia module 238 may be implemented in hardware as part of the microcontroller 220, or as software/firmware instructions programmed into the device and executed on the microcontroller 220 during certain modes of operation. Such a module may include other capabilities related to other functions that may be germane to the dysautonomia. For example, such a module may include capabilities related to analysis of IEGMs (e.g., slopes, amplitudes, etc.) and/or determining cardiac performance, especially as it may relate to one or more pacing parameters.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer (e.g., wireless communication, etc.). The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, M delay, AV delay, W delay, etc.) at which the atrial and ventricular pulse generators, 222 and 224, generate stimulation pulses. A cardiac output sensor optionally provides information to the dysautonomia module 238 for orthostatic control.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down. Such information is optionally used by the dysautonomia module 238 for orthostatic control.

The stimulation device 100 optionally includes circuitry capable of sensing heart sounds and/or vibration associated with events that produce heart sounds. Such information is optionally used by the dysautonomia module 238 for orthostatic control. Circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having microcircuitry on a tiny silicon chip into which some mechanical device such as a mirror or a sensor has been manufactured. The aforementioned ADXL202 MEMS includes micro-circuitry and a mechanical oscillator.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. Such impedance information is optionally used by the dysautonomia module 238 for orthostatic control.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses. Shocking optionally relies on information related to orthostatic control (e.g., whether control is failing, a change has initiated arrhythmia, etc.).

Figure 3:
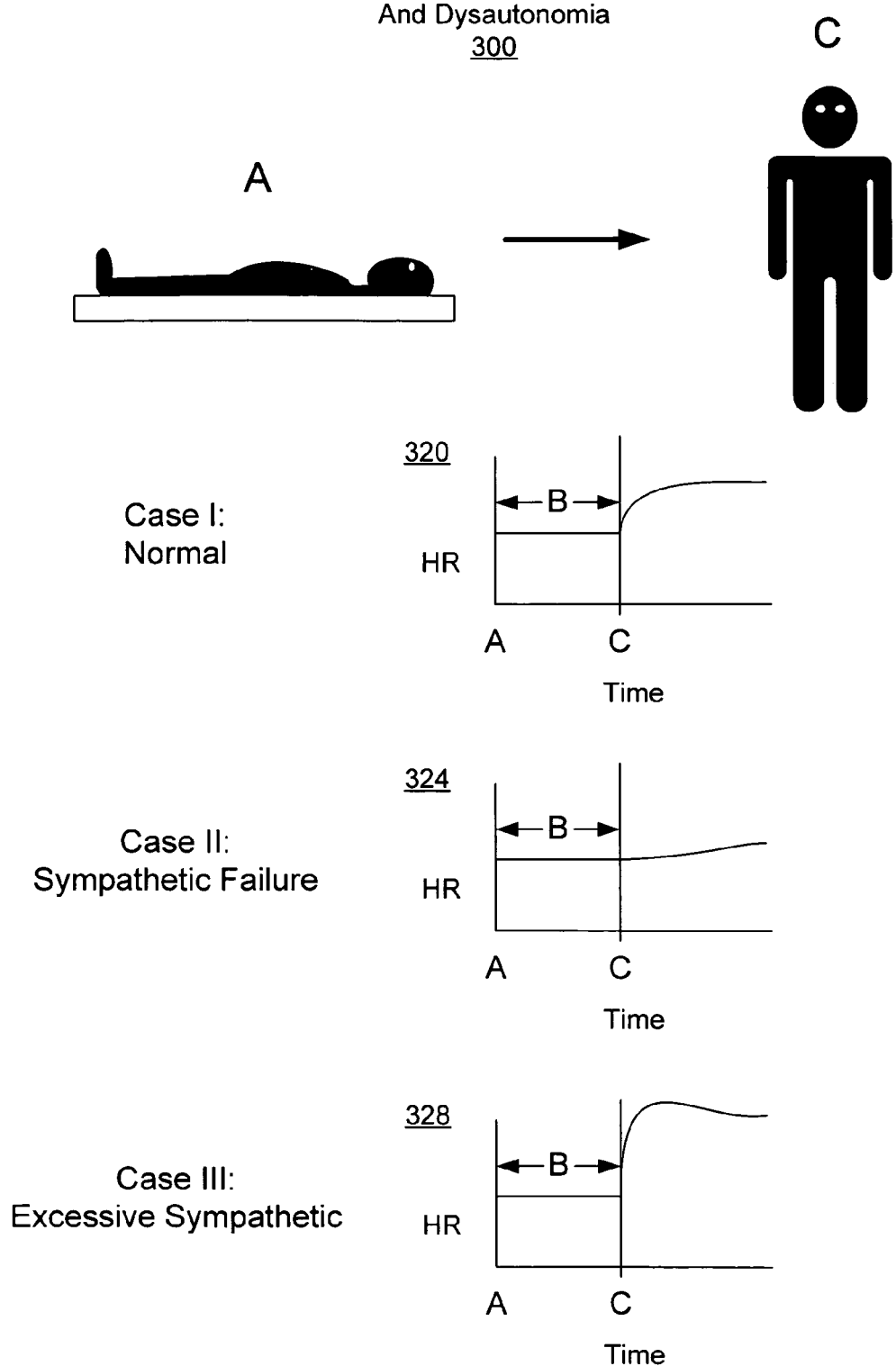
FIG. 3 is a schematic of patient position change and various possible physiological responses thereto.

FIG. 3 shows a schematic 300 of possible physiological responses to a change in patient position. The schematic 300 includes a patient in supine position (A) moving to a prone position (C). In a plot 320 of heart rate (HR) versus time, heart rate increases when the patient moves to the prone position (C) after some duration (B) in the supine position (A). The increase in heart rate is representative of a normal autonomic system response to the change in position where sympathetic activity increases to cause an increase in heart rate (Case I: Normal). A shift in autonomic balance toward sympathetic by reduced parasympathetic activity may also cause an increase in heart rate. In either instance, the resulting increase in heart rate aims to maintain an adequate supply of blood to the brain and to reduce pooling of blood in the lower extremities.

Another plot 324 of heart rate (HR) versus time indicates an abnormal response to a change in patient position (Case II: Sympathetic Failure). In moving to a prone position (C) after some duration (B) in the supine position (A), heart rate does not increase immediately. Consequently, the patient is at risk of syncope (i.e., fainting). The inadequate autonomic response (sympathetic failure) is a type of dysautonomia.

Yet another plot 328 of heart rate (HR) versus time indicates another abnormal response to a change in patient position (Case III: Excessive Sympathetic). In moving to a prone position (C) after some duration (B) in the supine position (A), heart rate increases excessively. The excessive surge in sympathetic activity, or shift to an excessively sympathetic autonomic balance, is another type of dysautonomia.

Sympathetic failure dysautonomia is very highly correlated with progressive congestive heart failure and renal disease due to complications of diabetes. Thus, as described herein, various exemplary mechanisms aim to compensate for or monitor sympathetic failure dysautonomia. Other exemplary mechanisms aim to compensate for or monitor excessive sympathetic dysautonomia. Yet other exemplary mechanisms aim to compensate for or monitor various types of dysautonomia.

Figure 4:
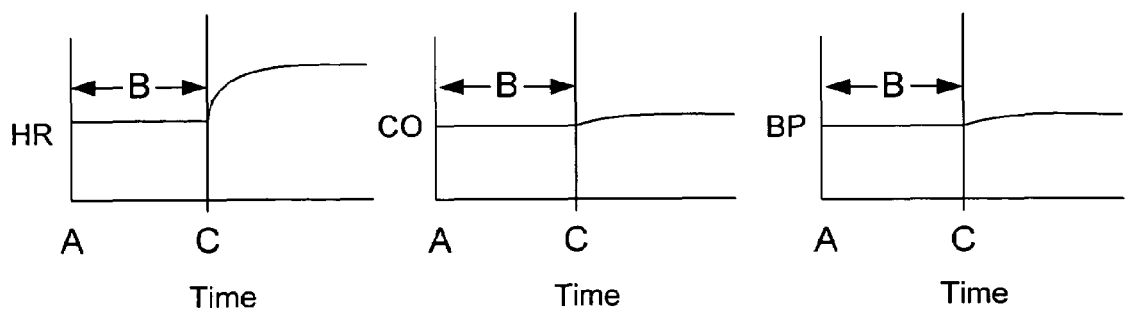
FIG. 4 is a series of plots of physiological responses that correspond to various cases presented in FIG. 3.
Figure 4:
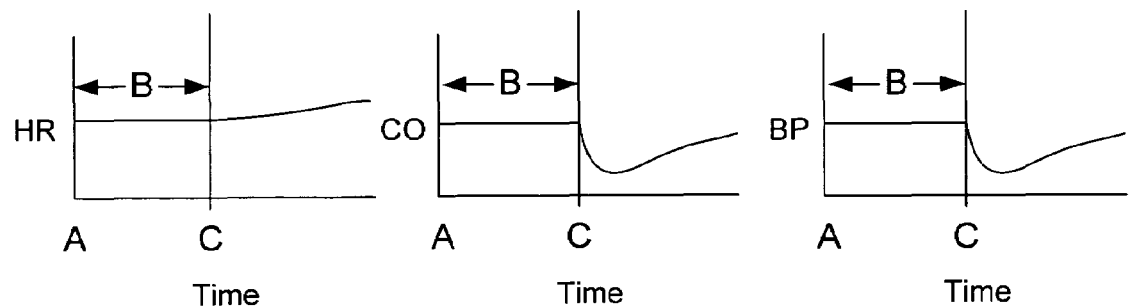
Figure 4:
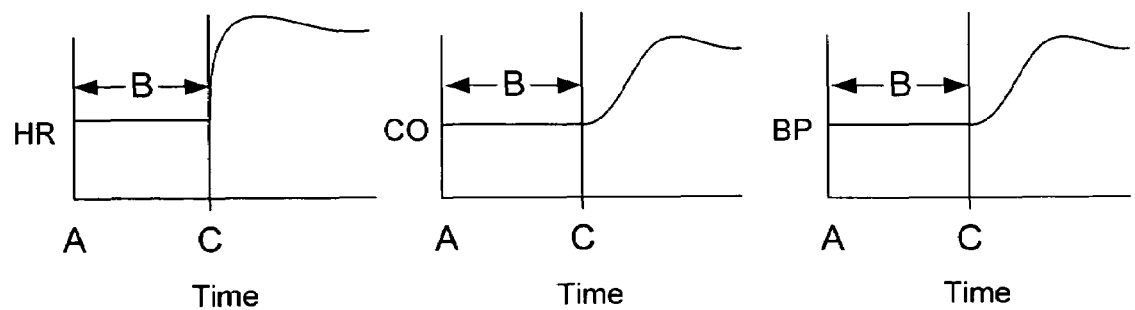

FIG. 4 shows various plots 400 of possible physiological responses related to the three cases (Case I, II and III) of FIG. 3. In Case I (Normal), a series of plots 420 show how heart rate (HR), cardiac output (CO) and blood pressure (BP) may vary when a patient moves to a prone position (C) after some duration (B) in a supine position (A). As described with respect to Case I of FIG. 3, heart rate increases due to sympathetic activity. In turn, the increase in heart rate maintains cardiac output and blood pressure.

In Case II (Sympathetic Failure), the lack of sympathetic activity immediately after a change to a prone position (C) causes a drop in cardiac output (CO) and a drop in blood pressure (BP). Such a sympathetic failure may be defined as "orthostatic hypotension", which is usually associated with a drop of greater than about 20 mmHg in systolic blood pressure over a three minute period following a significant change in postural position or a drop of greater than about 10 mmHg in diastolic blood pressure. In patients with orthostatic hypotension, the most severe decline in cardiac output occurs in about the first 30 seconds to about one minute after a change in patient position. Various exemplary mechanisms aim to increase heart rate where sympathetic response is inadequate. For example, pacing may be used to increase heart rate or autonomic stimulation may be used to inhibit parasympathetic activity or to increase sympathetic activity.

In Case III (Excessive Sympathetic), the excessive sympathetic activity after a change to a prone position (C) causes an increase in cardiac output (CO) and an increase in blood pressure (BP). As described herein, various exemplary mechanisms aim to increase parasympathetic activity or decrease sympathetic activity to compensate for the excessive sympathetic activity. Various exemplary mechanisms aim to cause some form of AV block (optionally with ventricular pacing) to thereby slow heart rate where excessive sympathetic activity occurs.

Figure 5:
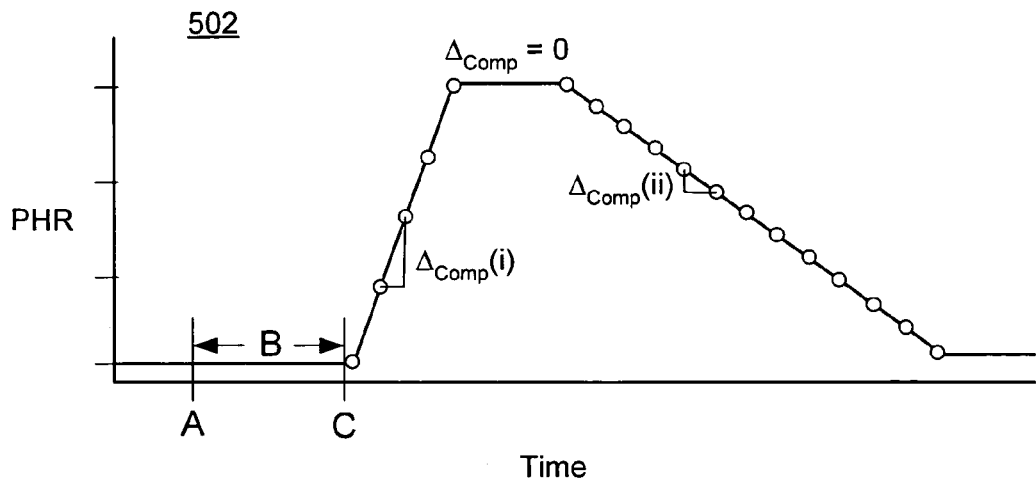
FIG. 5 is a conventional scheme for orthostatic hypotension compensation that includes a plot and a block diagram of a conventional method.
Figure 5:
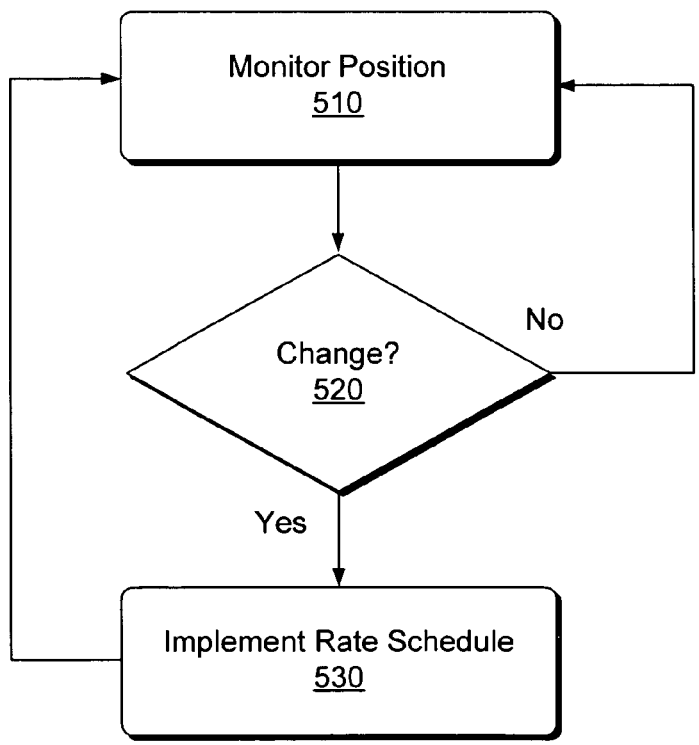

Some conventional pacing devices implement an orthostatic hypotension algorithm to compensate for an inadequate increase in heart rate. FIG. 5 shows a conventional algorithm 500. A plot 502 of paced heart rate (PHR) versus time indicates that paced heart rate increases after a patient moves to a prone position (C) after some duration (B) in a supine position (A), noting that the duration may be a predetermined time in such a conventional algorithm. The plot 502 includes three distinct and predetermined paced regions responsive to the change in patient position. In a first region, the paced heart rate increases linearly ($\Delta_{Comp}=\Delta_{Comp}(i)$). In a second region, the paced heart rate is constant ($\Delta_{Comp}=0$). In a third region, the paced heart rate decreases linearly ($\Delta_{Comp}=\Delta_{Comp}(ii)$). In this conventional orthostatic hypotension compensation algorithm, the adjustments occur according to a predetermined schedule.

A block diagram of the conventional method 504 includes a monitor block 510 that monitors patient position. A decision block 520 decides if a change in position has occurred. If the patient position changes, then the method 504 enters an implementation block 530 that uses a predetermined paced heart rate schedule to adjust the paced heart rate (see, e.g., the plot 502). If the patient position does not change, then the method 504 continues to monitor patient position in the monitor block 510.

The conventional method of FIG. 5 may increase paced heart rate when no increase is needed. More specifically, the conventional method of FIG. 5 relies only on a change in patient position after some duration; however, such a change may not result in a drop in blood pressure or cardiac output. Increasing paced heart rate where no need exists, wastes energy and may cause patient discomfort or alarm. Thus, various exemplary mechanisms described herein aim to avoid unnecessary adjustment to paced heart rate.

Figure 6:
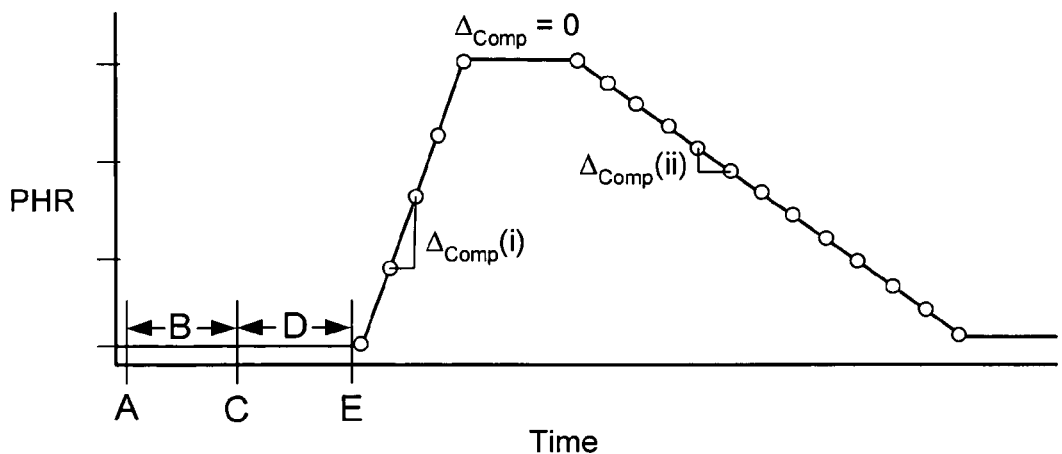
FIG. 6 is an exemplary scheme for orthostatic hypotension compensation that includes a plot and a block diagram of an exemplary method.
Figure 6:
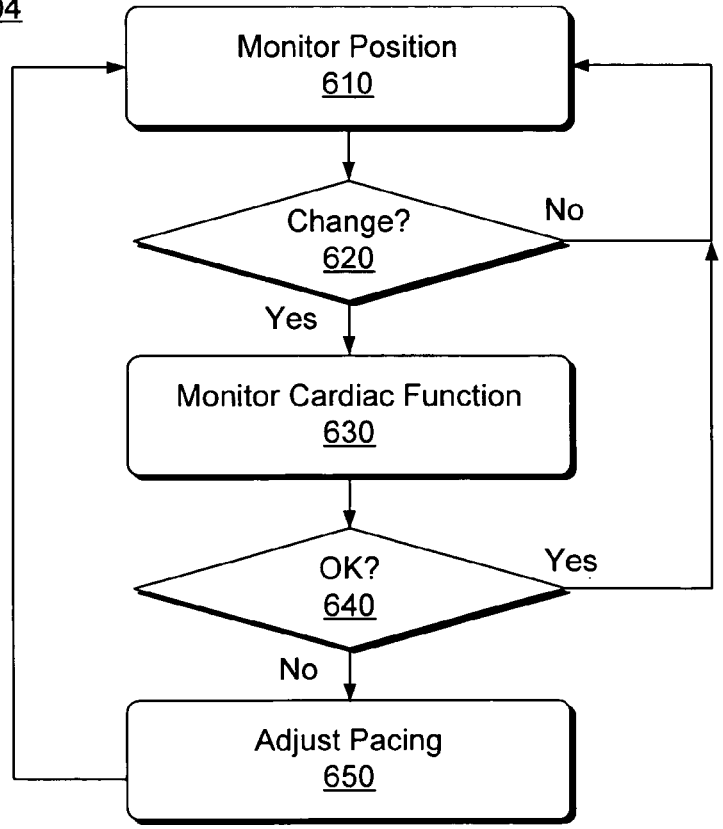

FIG. 6 shows an exemplary mechanism 600 that aims to at least avoid unnecessary increases in heart rate. A plot 602 of paced heart rate (PHR) versus time indicates that a second duration (D) occurs after a patient changes position (C). The second duration (D) allows for acquisition of or analysis of patient physiology. For example, during the duration (D), acquisition and analysis of information related to cardiac output may occur and, based on such information and analysis, a decision to increase paced heart rate may be made (E). Thus, the second duration (D), which extends from the change in position (C) to a decision (E), may be viewed as a confirmation window to confirm whether an increase in paced heart rate is warranted.

The plot 602 indicates that a decision to increase paced heart rate was made (E). At this point in time, the paced heart rate may be adjusted as in the conventional algorithm 500. Alternatively, as described in more detail below, the information or analysis related to cardiac output may be used to select a schedule or otherwise adjust paced heart rate (i.e., duration or rate).

A block diagram of such an exemplary method 604 includes a monitor block 610 that monitors patient position. A decision block 620 decides if a change in position has occurred. If the patient position changes, then the method 604 monitors cardiac function in a monitor block 630. Another decision block 640 then decides if the cardiac function is OK. If the cardiac function is OK, then there is no need to increase the paced heart rate and the method 604 returns to the patient position monitoring block 610. However, if the cardiac function is not OK, then the method 604 enters an adjustment block 650 that adjusts the paced heart rate.

Figure 7:
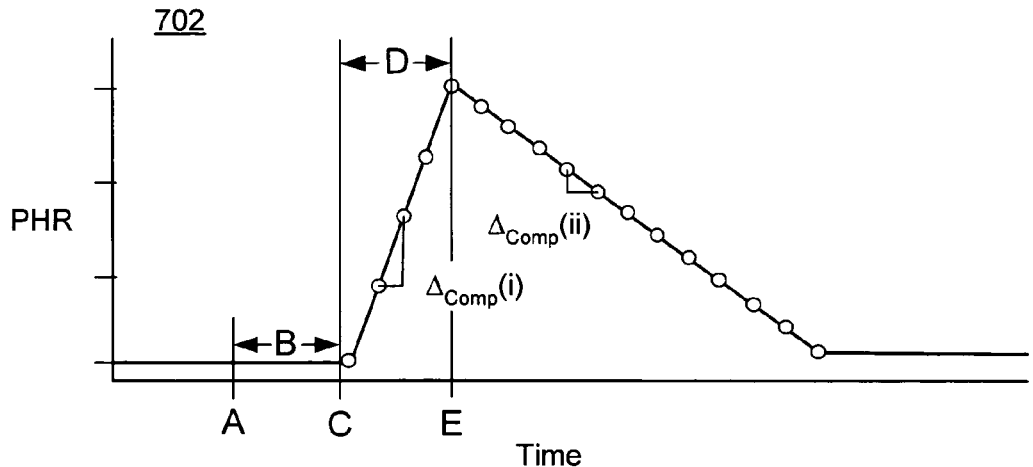
FIG. 7 is another exemplary scheme for orthostatic hypotension compensation that includes a plot and a block diagram of an exemplary method.
Figure 7:
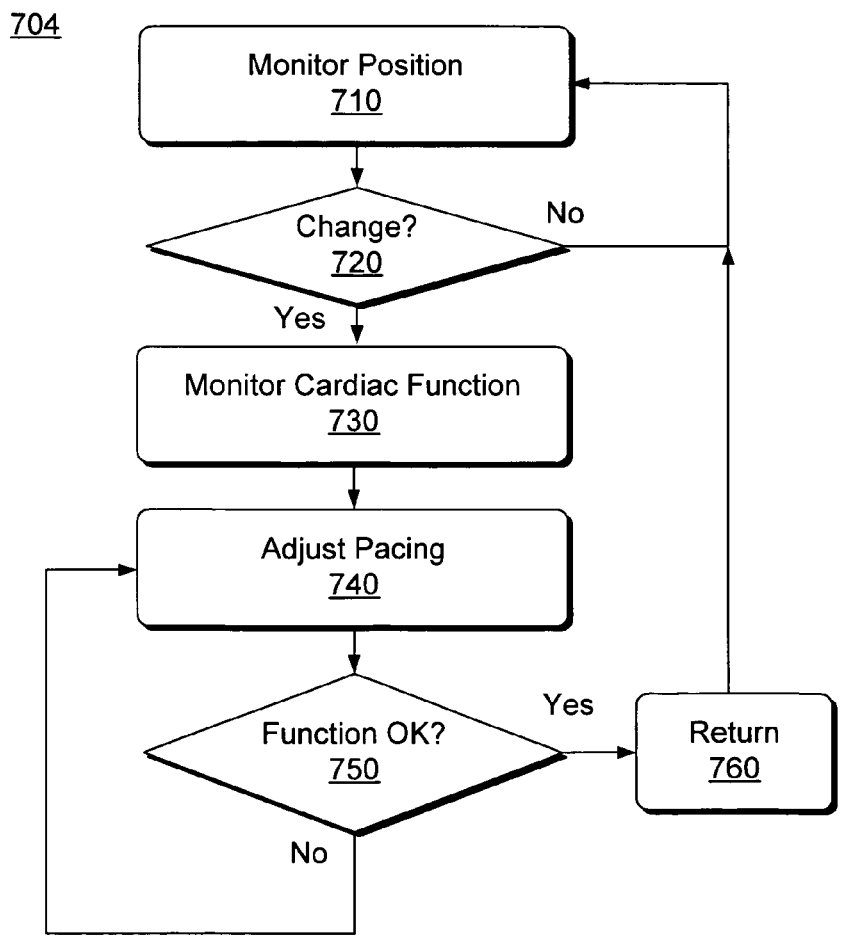

FIG. 7 shows an exemplary mechanism 700 that aims to adjust paced heart rate based on information related to cardiac function (e.g., cardiac output, blood pressure, etc.). A plot 702 of paced heart rate (PHR) versus time indicates that a second duration (D) occurs after a patient changes position (C); however, adjustment to paced heart rate commences after the first duration (B). The second duration (D) allows for acquisition of or analysis of patient physiology and adjustment of paced heart rate. For example, during the duration (D), acquisition and analysis of information related to cardiac output may occur and, based on such information and analysis, a decision to increase paced heart rate may be made during the duration (D). Further, information acquired during the duration (D) may be used to make adjustments to the paced heart rate after expiration of the duration (D). Thus, in this example, the second duration (D), which extends from the change in position (C) to some point in time (E), may be viewed as a data acquisition window to acquire information related to cardiac function. Such information may be used to select a schedule or otherwise adjust paced heart rate (i.e., duration or rate).

A block diagram of such an exemplary method 704 includes a monitor block 710 that monitors patient position. A decision block 720 decides if a change in position has occurred. If the patient position changes, then the method 704 monitors cardiac function in a monitor block 730. An adjustment block 740 follows that optionally adjusts paced heart rate. Monitoring of cardiac function continues for some period of time (see, e.g., the duration (D) in the plot 702). Another decision block 750 then decides if the cardiac function is OK. If the cardiac function is OK, then the method 704 enters a return block 760, which may implement further adjustments to paced heart rate or simply return to the monitoring block 710. However, if the cardiac function is not OK, then the method 704 continues at the adjustment block 740 to further adjust the paced heart rate.

Figure 8:
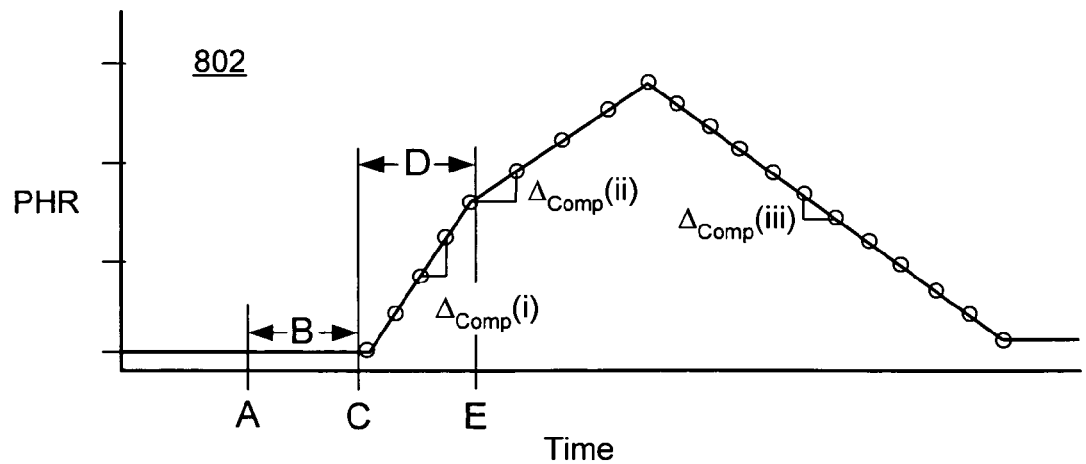
FIG. 8 is a series of plots of paced heart rate versus time for exemplary methods of adjusting paced heart rate based on information related to cardiac output.
Figure 8:
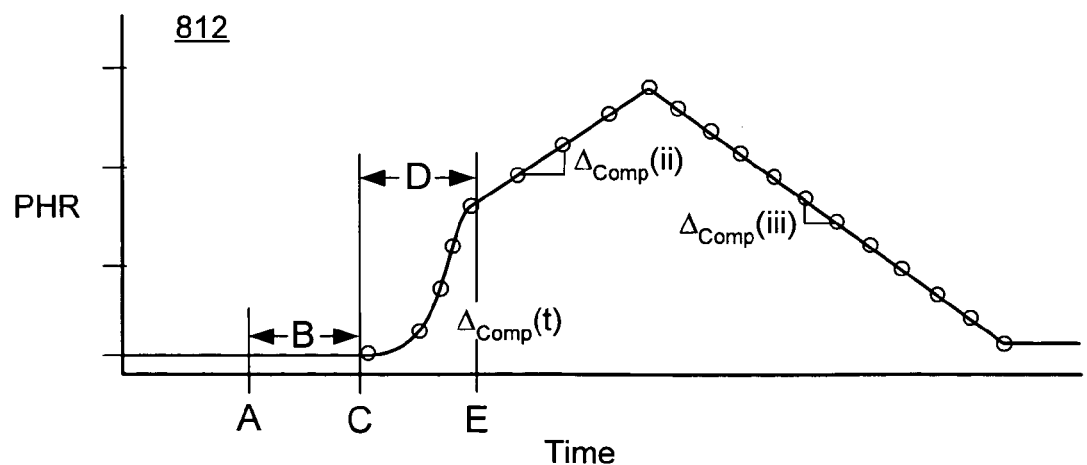

FIG. 8 shows several plots 800 of exemplary mechanisms that aim to adjust paced heart rate based on information related to cardiac function (e.g., cardiac output, blood pressure, etc.). A plot 802 of paced heart rate (PHR) versus time indicates that a second duration (D) occurs after a patient changes position (C) where adjustment to paced heart rate commences after the first duration (B). The second duration (D) allows for acquisition of or analysis of patient physiology and adjustment of paced heart rate. For example, during the duration (D), acquisition and analysis of information related to cardiac output may occur and, based on such information and analysis, a decision to increase paced heart rate may be made during the duration (D). Further, information acquired during the duration (D) may be used to make adjustments to the paced heart rate after expiration of the duration (D). Thus, in this example, the second duration (D), which extends from the change in position (C) to some point in time (E), may be viewed as a data acquisition window to acquire information related to cardiac function. Such information may be used to select a schedule or otherwise adjust paced heart rate (i.e., duration or rate) as indicated by the linear increase $\Delta_{Comp}(ii)$ or $\Delta_{Comp}(iii)$, which occur after time (E).

Another plot 812 of paced heart rate (PHR) versus time indicates that a second duration (D) occurs after a patient changes position (C) where adjustment to paced heart rate commences after the first duration (B) in a linear or non-linear manner. Such adjustment to paced heart rate may rely on proportional, integral or derivative (PID) control or other form of control.

An exemplary mechanism may therefore use a feedback loop to dynamically adjust the paced heart rate depending on cardiac output as an independent variable. In such an example, as a patient moves from a rest state to an active state (e.g., as indicated by patient position or other information), and a change in cardiac output is detected, the paced heart rate delivered to the patient is adjusted to maintain the cardiac output required for an active state. Such an exemplary mechanism may alternatively aim to maintain the cardiac output that existed during the patient's rest state.

In one example, a feedback loop adjusts the next delivered pace to reduce the difference between the previous (rest state or predetermined active state) cardiac output and the presently measured cardiac output. A pacing schedule may be applied and the mechanism may determine whether the cardiac output has stabilized at a predetermined output level. If not, the mechanism may measure the next state of cardiac output, and adjusts the pacing schedule in another attempt to match and stabilize the cardiac output.

A care provider may tune such an exemplary control mechanism for the orthostatic cardiac output paced rate during tilt testing for the patient. For example, during tilt testing, a care provider may produce orthostatic hypotension responses from the patient. In this example, a number of initial hypotension events can be used to tune a proportional gain factor ($K_p$); a number of next hypotension events can be used to adjust a derivative gain factor ($T_d$), which acts to dampen overshoot of the proportional control; and, hypotension events can be used to adjust an integral gain factor ($1/T_i$) for purposes of final value offset. A care provider may repeat such a process one or more times, until the PID controller accurately and quickly responds to the orthostatic hypotension event.

In general, tuning of a PID controller may start by removing all integral and derivative action (i.e., setting $T_d=0$ and $1/T_i=0$). The proportional gain factor (i.e., $K_p$) can then be tuned to give a desired response, ignoring any final value offset from the set-point. A further increase in the proportional gain factor may be made and then the derivative factor tuned to dampen overshoot. Next, the integral gain factor may be adjusted to remove any final value offset. The process may be repeated as necessary to achieve as large as possible proportional gain.

Figure 9:
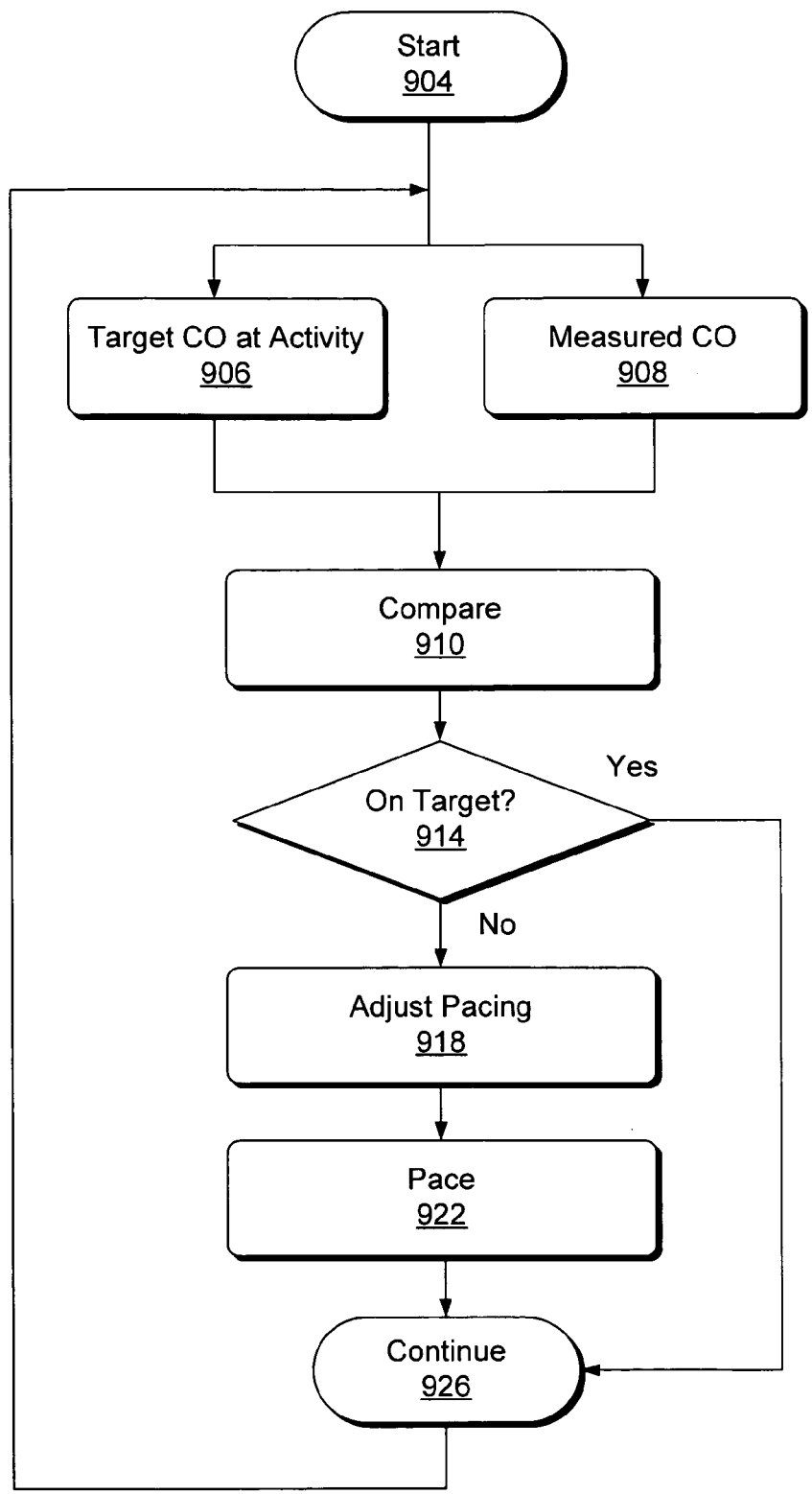
FIG. 9 is a block diagram of an exemplary method that compares a measured cardiac output to a target cardiac output.

FIG. 9 shows a block diagram of an exemplary method 900 that relies on a target cardiac output and a measured cardiac output to adjust paced heart rate in response to a change in patient position. The method 900 commences in a start block 904, which may be triggered by a change in patient position, activity, etc. Next, a target cardiac output for the patient state (e.g., position, activity, etc.), is input 906 and a measured cardiac output is input 908. A comparison block 910 follows that compares the target and the measured cardiac output. A decision block 914 decides if the measured cardiac output is "on target", for example, within some small range of the target value. If the decision block 914 decides that the cardiac output is on target, then the method 900 continues at a continuation block 926 that optionally enters a subsequent loop.

If the decision block 914 decides that the measured cardiac output is not "on target", i.e., too large of an error exists between the target value and the measured value, then the method continues in an adjustment block 918 that adjusts paced heart rate. A delivery block 922 follows that delivers a pace to the heart according to the paced heart rate of the adjustment block 918. The method 900 then continues at the continuation block 926. Further loops may occur as required.

Figure 10:
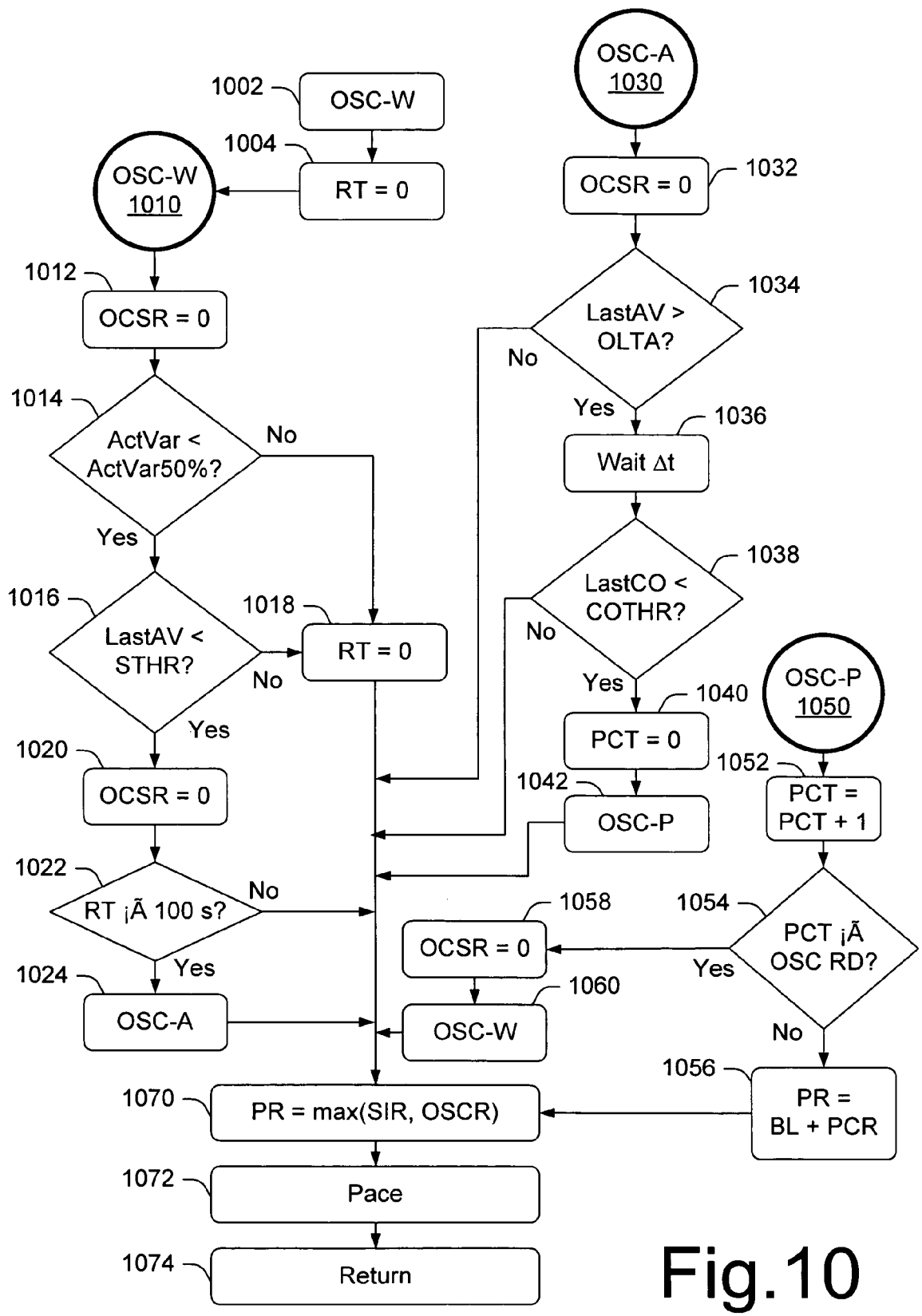
FIG. 10 is a block diagram of an exemplary scheme that includes various states related to pacing.

FIG. 10 shows a diagram of an exemplary scheme 1000 of various exemplary orthostatic compensation states. The states include an orthostatic compensation wait state 1010 (OSC-W), an orthostatic compensation alert state 1030 (OSC-A) and an orthostatic compensation pace state 1050 (OSC-P). Action and state depend in part on an orthostatic long term running average (OLTA), a short term cardiac output (LastCO), an orthostatic cardiac output average (CO-THR), an orthostatic threshold offset value, filtered activity variance (ActVar), activity short term running average (LastAV), and an activity long term running average (STHR). The OLTA can be set to equal the STHR+a programmed "OSR Threshold Offset" value.

In general, if an orthostatic response (OSR) rate parameter is programmed to a value other than "off", an exemplary implantable device such as the device 100 performs according to the exemplary scheme 1000.

With respect to the wait state 1010, in a state set block 1002, the state is set to OSC-W. A rest time set block 1004 sets a rest time (RT) parameter to zero. The scheme 1000 then proceeds according to the wait state 1010. In the wait state 1010, an orthostatic compensation rate (OSCR) set block 1012 sets the OSCR to zero. A decision block 1014 follows that decides if the ActVar is less than a parameter ActVar50%. The value of ActVar50% may be determined by using an activity variance histogram or other historical activity information. For example, where a histogram is used, bin counts are added, starting from the lowest bin and continuing up until a count of 10112 (or 50%) is reached. The bin number when this count is reached is set to the ActVar50%. If the decision block 1014 decides that ActVar is less than ActVar50%, then the OSC-W state 1010 continues in another decision block 1016 that decides if LastAV is less than STHR. However, if the decision block 1014 decides that ActVar is not less than ActVar50%, the process continues in a rest time set block 1018 that sets RT=0. The paced heart rate is then set according to a set block 1070, which can be entered by the OSC-W state 1010, the OSC-A state 1030 and the OSC-P state 1050.

If the decision block 1016 decides that the LastAV is less than the STHR, then the OSC-W state 1010 process continues in a set block 1020 that sets the OSCR to zero. Yet another decision block 1022 follows that decides if the rest time has exceeded a set time. For example, if the rest time meets or exceeds about 100 seconds, then the process continues in an OSC-A state set block 1024. However, if the rest time does not meet or exceed the value, then the process continues at the paced heart rate set block 1070, noting that the change in state also leads the process to the paced heart rate set block 1070.

The OSC-A state 1030 performs a process whereby a set block 1032 sets the OSCR to zero. A decision block 1034 follows that decides if the LastAV exceeds the OLTA. If it does not, the process continues at the paced heart rate set block 1070. However, if the LastAV exceeds the OLTA, then the process continues in a wait block 1036, which may wait a time ranging from a fraction of a second to about 10 seconds. After the wait block 1036, another decision block 1038 decides if a last cardiac output value (LastCO) is less than the orthostatic cardiac output average (COTHR). If the LastCO is not less than the COTHR, the process proceeds to the paced heart rate set block 1070. However, if the LastCO is less than the COTHR, then a set block 1040 sets a pace counter (PCT) to zero and a state set block 1042 sets the state to OSC-P 1050. Thereafter, the process continues to the paced heart rate set block 1070. Thus, the exemplary OSC-A state 1030 includes a mechanism for deciding if cardiac output is insufficient. And, in response to an insufficient cardiac output, the exemplary OSC-A state 1030 transitions to the OSC-P state 1050 where orthostatic response pacing is initiated (e.g., under certain circumstances as may be decided by the PCT decision block 1054).

The OSC-P state 1050 performs a process that increments the aforementioned pace counter (PCT). A decision block 1054 decides if the PCT is greater than or equal to an OSC response duration (OSC RD). If the PCT is less than the OSC RD, then the process continues in a set block 1056 that sets the paced rate (PR) to a baseline rate (BL) plus an OSC response rate based on pace count (PCR). The process then continues at the paced heart rate set block 1070. However, if the decision block decides that the PCT exceeds the OSC RD, then a set block 1058 sets the OSCR to zero and a state set block 1060 sets the state to OSC-W 1010. The process then enters the paced heart rate set block 1070.

According to the exemplary scheme 1000, at every pacing cycle, ActVar is compared with ActVar50% and LastAV is compared with OLTA. Rest Time (RT) is the duration when ActVar is less than ActVar50% and when LastAV is less than OLTA. If the Rest Time (RT) duration is greater than zero, it is reset when ActVar is greater than or equal to ActVar50% or when LastAV is greater than or equal to OLTA. If Rest Time (RT) is greater than or equal to a duration of about 100 seconds (see the decision block 1022), the device shall enter the OSR-A state 1030 (per the set block 1024).

Once LastAV is greater than OLTA and the exemplary scheme 1000 is in the OSC-A state 1030, an increase in the current pacing rate to an appropriate orthostatic response (OSR) rate can occur. For example, the OSR indicated rate can be increased from the current pacing rate to the OSR rate by adding an appropriate delta value each pacing cycle until the rate reaches some limit. The delta value may be calculated once only, based on the initial current pacing rate, when the LastAV condition is met. In other examples, the delta may be determined pace-by-pace or on some other basis (see, e.g., the plot 812 of FIG. 8). Fractional results can be truncated and if the initial current pacing rate is greater than the OSR rate, then delta will not be used and the OSR indicated rate will equal the OSR rate. Pacing at the OSR rate may continue for some duration. Upon expiration of such an OSR duration, the process may return to a programmed base rate. In one example, a rate redaction occurs at about 2.5 ppm per pacing cycle. If another rate modifying algorithm is active concurrently with the Orthostatic Response mechanism, the higher indicated rate will normally be used. Such a decision may occur in the paced heart rate set block 1070. When the OSR indicated rate is reduced back to the base rate, orthostatic response detection may continue. A delivery block 1072 calls for delivery of the pace and a return block 1074 returns the exemplary scheme 1000 to the appropriate state.

Figure 11:
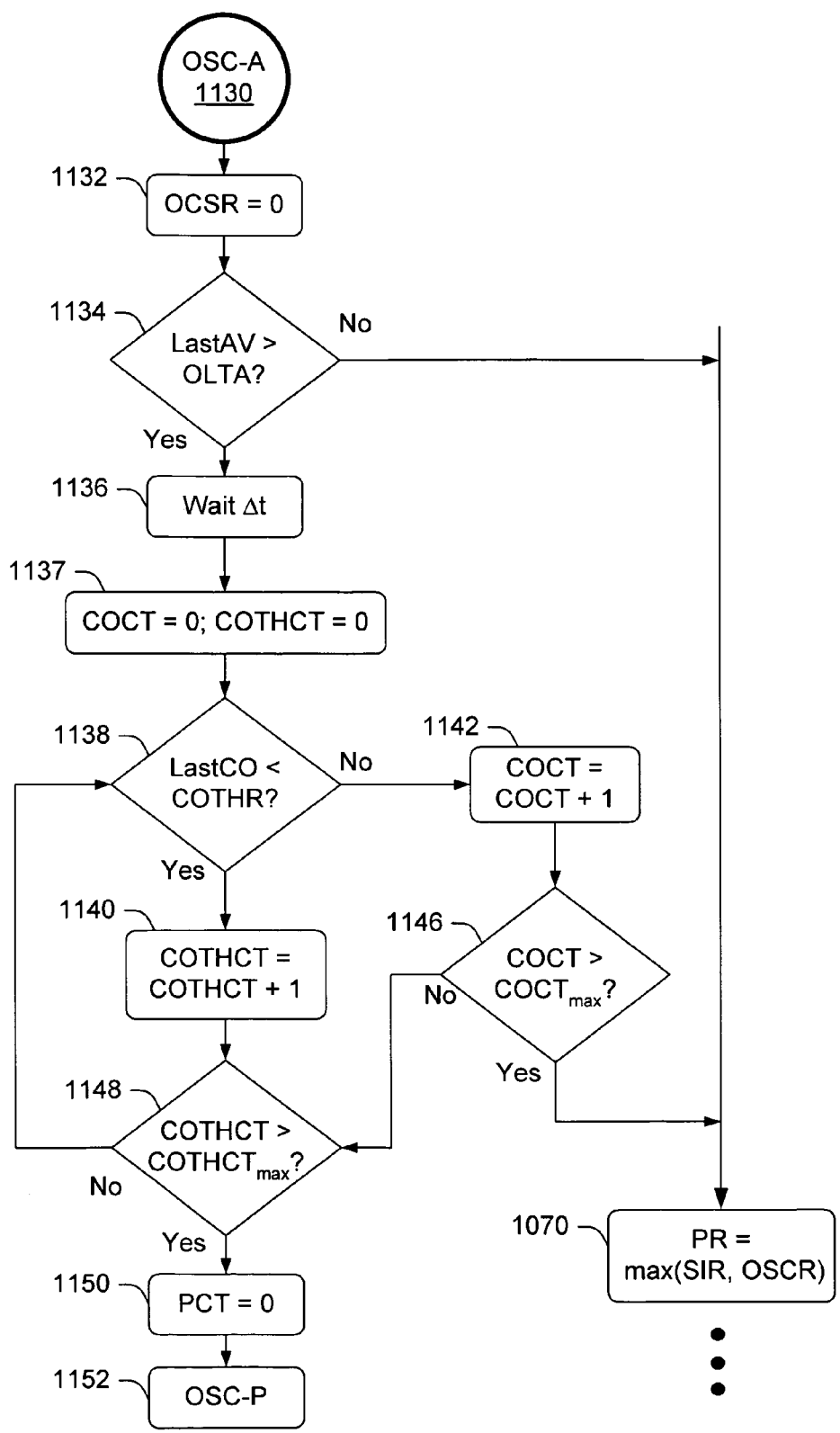
FIG. 11 is a block diagram of an exemplary process for an orthostatic compensation alert state suitable for use in the exemplary scheme of FIG. 10.

FIG. 11 shows another exemplary OSC-A state 1130. In comparison to the exemplary OSC-A state 1030, the OSC-A state 1130 does not change the state from OSC-A to OSC-P unless the drop in cardiac output continues for a predetermined length of time. In this way, an exemplary implantable pacing device (e.g., a pacemaker or pacemaker/ICD) does not inappropriately begin the response rate pacing if a significant change in measured cardiac output only occurs momentarily, and is reestablished to a normal level within a short period of time.

As shown in FIG. 11, the exemplary OSC-A state 1130 includes blocks 1137, 1140, 1142, 1146 and 1148, which do not appear in the exemplary OSC-A state 1030 of FIG. 10. The set block 1037 sets two counters to zero: a cardiac output counter (COCT) and a cardiac output threshold counter (COTHCT). COCT marks the amount of time (via counts) during which the process monitors for a significant drop in cardiac output while COTHCT marks the number of times the cardiac output measurement is less than COTHR, the cardiac output threshold for significant change.

As in 1030, a decision block 1138 decides if the LastCO is less than COTHR. In response to the decision, the COCT counter or the COTHCT counter is incremented, blocks 1142, 1140, respectively. Another decision block 1146 decides if COCT exceeds a maximum count value and yet another decision block 1148 decides if COTHCT exceeds a maximum count value. If COTHCT exceeds the maximum count, then a set block 1150 sets a pace counter (PCT) to zero and a state set block 1152 sets the state to OCS-P (e.g., 1050 of FIG. 10). If the COCT count exceeds the maximum count, then the process continues at the paced heart rate set block 1070, which as already mentioned may select the maximum of the orthostatic compensation rate and any other rate that may be in competition with the orthostatic compensation mechanism.

Figure 12:
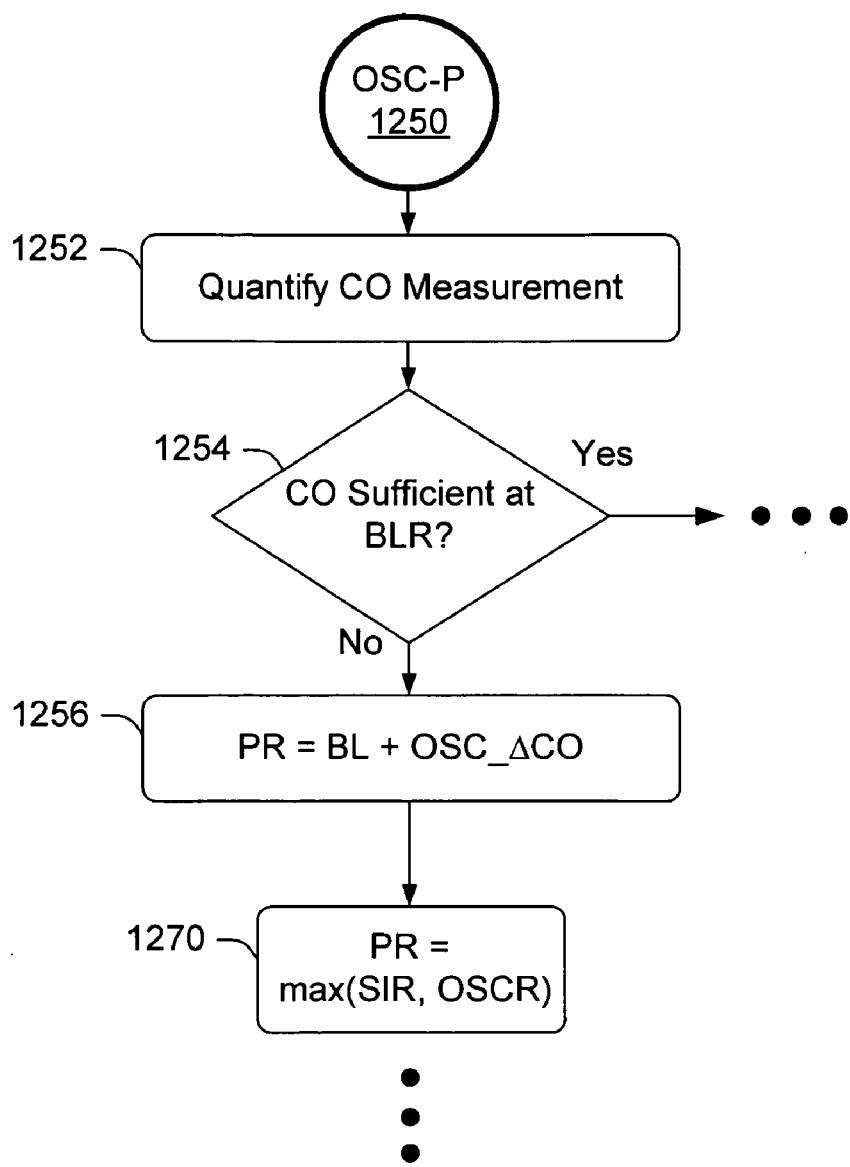
FIG. 12 is a block diagram of an exemplary process for an orthostatic compensation pace state suitable for use in the exemplary scheme of FIG. 10.

FIG. 12 shows a diagram of an exemplary OSC-P state process 1250. The exemplary process 1250 determines a paced heart rate based on a cardiac output. In particular, a cardiac output value may be used to determine an appropriate pacing rate. The exemplary OSC-P state process 1250 may be part of an exemplary feedback loop control system that optionally relies on proportional, derivative or integral control. Thus, in this example, the process 1250 may incorporate a PID controller to dynamically adjust the cardiac output through a response rate schedule that is controlled. A dynamic response rate schedule or schedules can replace a fixed or predetermined rate schedule or schedules.

As shown in FIG. 12, a quantification block 1252 quantifies one or more cardiac output measurements. A decision block 1254 decides if cardiac output is sufficient at a given baseline heart rate. If the cardiac output is sufficient, then the process continues, as appropriate (see, e.g., FIG. 10). However, if the output is insufficient, then a determination block 1256 determines a paced heart rate using the cardiac output or a cardiac output error (i.e., ΔCO). An adjustment value (OSC_ΔCO) may be added to a baseline value to thereby determine a paced heart rate that aims to compensate for orthostatic issues. The process continues in a paced heart rate set block 1270, which, as described above, may select the highest or most appropriate rate when more than one rate-setting mechanism is operating.

As mentioned with respect to FIGS. 3 and 4, excessive sympathetic activity may be triggered by a change in patient position or activity state. Sometimes the increase in heart rate is to an extent that a decrease in cardiac output results—a condition referred to as orthostatic intolerance. Orthostatic intolerance has the same conditions that indicate its initiation: a rapid change in posture, taking the patient from a resting state to an active state and a rapid drop in cardiac output. However, instead of no change in pacing rate, the patient has tachycardia, and possibly a tachyarrhythmia. Often, orthostatic intolerance is caused by the failure of a patient's baroreceptors to modulate the heart rate when initiated by the sudden posture and subsequent cardiac output changes.

To reduce the tachycardia caused by the orthostatic intolerance, a pacing lead is optionally placed at an appropriate afferent parasympathetic location (e.g., near the heart or remote from the heart), which is stimulated to increase parasympathetic activity and thereby reduce heart rate. Where such a lead is positioned near the heart, a set of pacing pulses may be used. One such afferent parasympathetic location is the carotid sinus. Other possible locations include the aorta and atria.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method of controlling a cardiac pacing rate, said method comprising:
   detecting a change in position;
   upon detecting a change in position, initiate adjusting the cardiac pacing rate, wherein an adjustment of the cardiac pacing rate is characterized by a rate of change as a function of time;
   measuring cardiac output after the detecting a change in position; and
   based at least in part on the measuring cardiac output, deciding whether to adjust the rate of change of the cardiac pacing rate.

2. The method of claim 1 wherein the change in position corresponds to a change from a supine position to a prone position.

3. The method of claim 1 further comprising tilt testing wherein the tilt testing includes measuring cardiac output.

4. The method of claim 1 wherein the deciding comprises comparing a measured cardiac output to a target cardiac output.

5. The method of claim 1 further comprising measuring intrinsic heart rate after the detecting a change in position.

6. The method of claim 5 further comprising calling for parasympathetic nerve stimulation.

7. The method of claim 1 further comprising, based at least in part on the measuring cardiac output, deciding whether to call for autonomic nerve stimulation.

8. The method of claim 1 further comprising detecting a change in activity.

9. The method of claim 1 further comprising determining the adjustment in cardiac pacing rate based at least in part on proportional, integral or derivative control.

10. The method of claim 1 further comprising repeating the measuring cardiac output and the deciding.

11. A method of controlling a cardiac pacing rate, said method comprising:
    detecting a change in activity;
    upon detecting a change in activity, initiate adjusting the cardiac pacing rate, wherein an adjustment of the cardiac pacing rate is characterized by a rate of change as a function of time;
    measuring cardiac output after the detecting a change in activity; and
    based at least in part on the measuring cardiac output, deciding whether to adjust the rate of change of the cardiac pacing rate.

12. The method of claim 11 wherein the change in activity corresponds to a change from a supine position to a prone position.

13. The method of claim 11 wherein the measuring cardiac output occurs for a predetermined duration after the detecting a change in position.

14. An implantable pacing apparatus comprising:
    a sensor operative to detect movement of a patient;
    a pacing circuit to deliver pacing stimuli to the patient at a cardiac pacing rate;
    a sensing circuit to acquire information related to cardiac output; and
    control logic to initiate adjusting the cardiac pacing rate upon movement of the patient, wherein an adjustment of the cardiac pacing rate is characterized by a rate of change as a function of time, and to determine cardiac output upon movement of the patient, and to decide whether to adjust the rate of change of the cardiac pacing rate based on the determined cardiac output.

15. The apparatus of claim 14 wherein the sensor comprises a patient position sensor and wherein the control logic increases the cardiac pacing rate if the patient position sensor indicates that the patient has moved to a prone position from a supine position and adjusts the rate of change of the cardiac pacing rate if the cardiac output does not satisfy a target cardiac output.

16. The apparatus of claim 14 wherein the sensor comprises an activity sensor.

* * * * *